US00PP14785P3

(12) United States Plant Patent
Orard

(10) Patent No.: US PP14,785 P3
(45) Date of Patent: May 18, 2004

(54) SHRUB ROSE PLANT NAMED 'ORAWICHKAY'

(50) Latin Name: *Rosa L.*
Varietal Denomination: Orawichkay

(75) Inventor: Pierre Orard, Feyzin (FR)

(73) Assignee: Edmunds' Roses, Wilsonville, OR (US)

( * ) Notice: Subject to any disclaimer, the term of this patent is extended or adjusted under 35 U.S.C. 154(b) by 44 days.

(21) Appl. No.: 10/012,656

(22) Filed: Nov. 5, 2001

(65) Prior Publication Data

US 2003/0088893 P1 May 8, 2003

(51) Int. Cl.[7] ..... A01H 5/00

(52) U.S. Cl. ..... Plt./103

(58) Field of Search ..... Plt./103, 110, 117, Plt./144, 124

*Primary Examiner*—Howard J. Locker

(74) *Attorney, Agent, or Firm*—Christie, Parker & Hale, LLP

(57) ABSTRACT

A new variety of shrub rose plant suitable for garden decoration, having flowers of white coloration.

1 Drawing Sheet

BACKGROUND OF THE INVENTION

This invention relates to a new and distinct variety of shrub Rose, *Rosa L.* The varietal denomination of the new variety is 'Orawichkay'. It has as its seed parent the unpatented variety known as 'DIComono' and as its pollen parent, an unnamed and unpatented cultivar of the species rose known as *Rosa wichuriana*. It is believed that botanically, the new variety would be classified as a hybrid species of *Rosa wichuriana.*

SUMMARY OF THE INVENTION

Among the features which distinguish the new variety from other presently available and known commercial rose cultivars are the following combination of characteristics: 'Orawichkay' bears small, pure white, single blooms with showy golden yellow stamens borne in large pyramidal clusters throughout the growing season.

The new variety is low, about ½ meter, and spreading, between about 1 to 1½ meters and bears small, Dark Green, lustrous foliage that shows good resistance to Powdery Mildew, Blackspot and Rust.

Since the variety is, for all practical purposes, sterile, no deadheading is required and the vitality of the new variety that would normally go to producing seed apparently is spent in producing more bloom. The fact that the blooms have virtually no scent does not in any way detract from its value as a landscape cultivar. The new variety is a bushy, spreading plant, suitable for outdoor garden decoration.

Asexual reproduction of the new variety by budding as performed in Clackamas County, Oregon shows that the foregoing and other distinguishing characteristics come true to form and are established and transmitted through succeeding propagations. 'Orawichkay' may be asexually propagated by cuttings, budding, grafting, layering or tissue culture. Budding and grafting have been successful on the major propagation understocks; namely, *Rosa multiflora, Rosa laxa,* and *Rosa canina*, as well as the cultivar known as 'Dr. Huey'.

COMPARISON WITH PARENTS

The new variety may be distinguished from its seed parent, 'DICimono' by the following combination of characteristics: 'DICimono' is a free blooming floribunda rose cultivar. The flowers of 'DICimono' are salmon pink and are well formed with about 35 petals. The seed parent variety is upright and slightly spreading.

The new variety may be distinguished from its unnamed *Rosa wichuriana* pollen parent, by the following combination of characteristics: (*Rosa wichuriana* is a species rose indigenous to Northeastern Asia). The pollen parent is nearly prostrate with creeping branches and has few flowers which are small, single to semi-double White and borne in pryamidal corybs only once in early summer.

BRIEF DESCRIPTION OF ILLUSTRATION

The accompanying photograph illustrates specimens of the new variety and shows the foliage and flowering from bud to full bloom depicted in color as nearly correct as it is possible to make in a color illustration of the character. Throughout this specification, color values are based upon The Colour Chart of The Royal Horticultural Society of London, England (1966), except where common terms of color definition are employed.

DESCRIPTION OF THE NEW VARIETY

The following description is of plants of the new variety grown outdoors in Wilsonville, Oreg. in the month of September. Phenotypic expression may vary with environmental, cultural and climatic conditions, as well as differences in conditions of light and soil.

FLOWER

The new variety usually bears its flowers in clusters of between about 5 to 25 per stem. Flowers are borne in regular pyramidal clusters on pendulous strong long stems (about 50 to about 75 cm). Outdoors, the plant blooms abundantly and nearly continuously during the growing season. The flowers have no fragrance.

BUD

The peduncle is about 1.5 to about 2 cm in length, of slender caliper, and usually erect. It is almost entirely covered with numerous stipitate glands, and very few hairs and prickles. Peduncle color is near between 144A and 144B.

Before the calyx breaks, the bud is about 0.5 to about 0.7 cm in diameter at the widest point, about 1.5 to about 1.8 cm in length, and pointed in shape with a conspicuous neck. The surface of the bud bears few foliaceous appendages and glandular bloom, usually with slender bristle-like foliaceous parts extending beyond the tip of the bud about ¼ or more of its length. Bud color is near between 143A and 143B. The outer surfaces of the sepals are glabrous with few hairs. Color is between 143A and 143B.

The inner surface of the sepals is covered with fine wooly tomentum; sepal margins are lined with few stipitate glands and hairs. Color of the inner surface of the sepals not covered by wooly tomentum is between 143B and 143C.

As the petals open (after the calyx breaks), the bud is between about 1 to about 1.2 cm in diameter at the widest point, about 1.5 to about 1.7 cm in length, and very pointed in form. The color of the under and upper surfaces of the newly opened petals is near between 158C and 158D. At the point where the petals attach, there is a very small zone near between 3B and 3C. The color of the upper surfaces of the newly opened petals is near between 155B and 155D. At the point where the petals attach, there is a very small zone of near 3C.

BLOOM

When fully open, the bloom ranges from about 6 to about 7.5 cm in diameter. Petalage is single with about 5 petals arranged regularly and no petaloids. When partially open, the bloom form is somewhat flat to cupped, and the petals are moderately flat to undulated. When fully open, the bloom form is more or less flat, and the petals are moderately flat to undulated.

PETALS

The substance of the petals is very crisp and thin, with upper surfaces slightly shiny to satiny and under surfaces slightly satiny. The petals are broadly round to obovate in shape with apices moderately rounded.

NEWLY OPENED FLOWER

The under and upper surface of the petals is near between 155B and 155D. At the point where the petals attach, there is a very small zone of near between 3B and 3C.

The general tonality of the newly opened flower is near near between 155B and 155D.

THREE-DAY OLD FLOWER

Color of the under and upper surface of the petals is near between 155B and 155D. At the point where the petals attach, there is a very small zone near between 3B and 3C.

The general tonality of the three-day old flower is near between 155B and 155D.

On the spent bloom, the petals usually drop off cleanly, fading to near between 155B and 155D, and are not particularly affected by cold, hot, wet, or dry weather.

In September in Wilsonville, Oreg., blooms on the bush growing outdoors generally last between about 1 to 2 to 4 days. Cut roses from plants grown outdoors and kept at normal indoor living temperatures generally last about 1 to 3 days.

MALE REPRODUCTIVE ORGANS

Stamens are average to many in number (approximately 100) and are arranged regularly about the pistils. The filaments vary in length and there are few without anthers. Filament color is near between 3C and 3D in color. The anthers are moderately small and all open approximately at the same time. Anther color is near between 16C and 16D when immature and near between 26A and 26B at maturity. Pollen is very sparse and near 26B in color.

FEMALE REPRODUCTIVE ORGANS

Pistils are few in number (approximately 12). The styles are moderately even, short in length, average to heavy in caliper, and moderately bunched to columnar. Stigma color is near between 154C and 154D. Style color is near between 144C and 144D. Ovaries are few, most all enclosed in the calyx.

Hips have not been observed on this variety when grown in Wilsonville, Oreg. Shortly after petal drop the peduncles dry, discolor and drop.

FOLIAGE

The compound leaves are usually comprised of between about 3 to 5 leaflets. The leaves are between about 8 to 12 cm in length and between about 4 to about 7 cm in width at the widest point, crisp in texture, and glossy in finish. The terminal leaflets are about 2.5 to about 4 cm in length and about 1.5 to about 3 cm in width at the widest point, shaped moderately ovate to oblong with moderately acute apices and very round bases. Margins are usually simply serrate.

The upper surface of the mature leaf is near between 137A and 137B. The under surface of the mature leaf is near between 138A and 138B. The upper surface of the young leaf is near 137C. The under surface of the young leaf is near 143B.

The rachis is small in caliper and moderately smooth. The upper side is shallowly grooved with few hairs and stipitate glands on the edges of the grooves. The under side of the rachis is very smooth with few hairs and stipitate glands.

The stipules are about 1.3 to about 1.5 cm in length and with long straight points that sometime turn out at an angle of less than 45 degrees.

The plant displays a high degree of resistance to Powdery Mildew and Blackspot and Rust as compared to other commercial varieties grown under comparable conditions in Wilsonville, Oreg. The microclimate of Oregon's Northern Willamette Valley in which Wilsonville is located is conducive to infestations of Rose Powdery Mildew in September when the photograph for the illustration was taken. The variety 'Orawichkay' will display symptoms of Rose Mildew at this time, particularly if unprotected by commercial fungicides.

GROWTH

The plant has a bushy spreading growth habit (between about 40 to about 60 cm in height and between about 100 to about 150 cm spread at the widest point), with full branching. It displays vigorous growth.

The color of the major stems is near between 143C and 144B. They bear a few large prickles that are between about 0.5 to about 0.7 cm in length. The large prickles are almost straight or hooked slightly downward with a short rounded base; prickle color is near between 178C and 178D. The major stem bears no small prickles. No hairs were observed.

The color of the branches is near between 143B and 143C. They bear a few prickles which are of similar size and shape to the large prickles on the major stems. The branches bear no small prickles. There are no hairs.

The color of the new shoots is near between 143C and 143D. They bear a few prickles which are of similar size and shape to the large prickles on the major stems; prickle color is near between 173C and 173D. The shoots bear no small prickles. No hairs were observed.

I claim:

1. A new and distinct shrub rose plant of the variety substantially as described and illustrated herein.

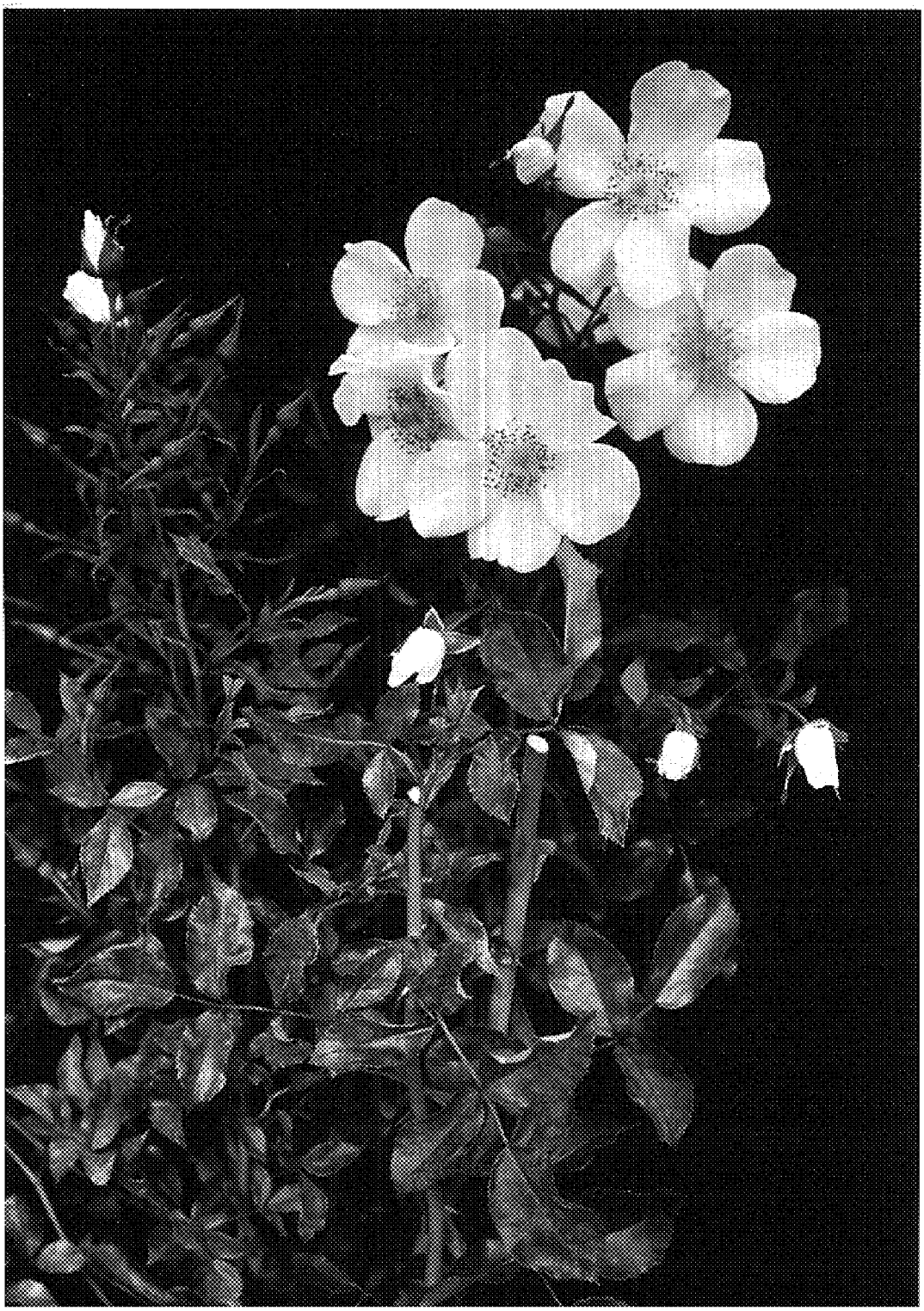

* * * * *